US009572569B2

(12) United States Patent
Maiorino et al.

(10) Patent No.: US 9,572,569 B2
(45) Date of Patent: Feb. 21, 2017

(54) SYSTEM AND METHOD FOR FORMING BARBS ON A SUTURE

(71) Applicant: Covidien LP, Mansfield, MA (US)

(72) Inventors: Nicholas Maiorino, Branford, CT (US); Timothy Kosa, Milford, CT (US); Mark Buchter, Orange, CT (US); Keith Kroeber, Portland, CT (US); Richard Casey Hart, Clinton, CT (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 14/603,487

(22) Filed: Jan. 23, 2015

(65) Prior Publication Data

US 2015/0135928 A1 May 21, 2015

Related U.S. Application Data

(63) Continuation of application No. 13/847,207, filed on Mar. 19, 2013, now Pat. No. 8,966,728, which is a (Continued)

(51) Int. Cl.
*A61B 17/06* (2006.01)
*A61B 17/04* (2006.01)
*A61B 17/00* (2006.01)

(52) U.S. Cl.
CPC ......... *A61B 17/06166* (2013.01); *A61B 17/04* (2013.01); *A61B 2017/00526* (2013.01); (Continued)

(58) Field of Classification Search
CPC .............. A61B 17/06166; A61B 17/04; A61B 2017/00526;A61B 2017/06176; Y10T 29/49998; Y10T 29/53991; Y10T 83/0207; Y10T 83/505; Y10T 83/0267; Y10T 83/04; Y10T 29/20
See application file for complete search history.

(56) References Cited

U.S. PATENT DOCUMENTS 6,241,747 B1 6/2001 Ruff
6,270,517 B1 8/2001 Brotz
(Continued)

FOREIGN PATENT DOCUMENTS

CN 101401735 A 4/2009
EP 2036502 A2 3/2009
(Continued)

OTHER PUBLICATIONS

European Search Report EP 10 25 0848 dated Jul. 26, 2013.
(Continued)

*Primary Examiner* — John C Hong

(57) ABSTRACT

A station for cutting a barb suture is provided. The barb cutting station includes a suture transport assembly for supporting a first suture, a first knife assembly for forming barbs on the first suture, and a first clamp and position assembly for approximating the at least first suture towards the at least first knife assembly. The barb cutting station may further include at least a first suture cutting mechanism configured for severing the at least first suture when a defect is detected. The station may also include at least a first visual inspection assembly configured for detecting defective barbs.

19 Claims, 6 Drawing Sheets

Related U.S. Application Data continuation of application No. 12/726,871, filed on Mar. 18, 2010, now Pat. No. 8,402,621.

(60) Provisional application No. 61/173,723, filed on Apr. 29, 2009.

(52) U.S. Cl.
CPC ..... *A61B 2017/06176* (2013.01); *Y10T 29/20* (2015.01); *Y10T 29/49998* (2015.01); *Y10T 29/53991* (2015.01); *Y10T 83/0207* (2015.04); *Y10T 83/0267* (2015.04); *Y10T 83/04* (2015.04); *Y10T 83/505* (2015.04)

(56) References Cited

U.S. PATENT DOCUMENTS

| | | | |
|---|---|---|---|
| 6,599,310 | B2 | 7/2003 | Leung et al. |
| 6,848,152 | B2 | 2/2005 | Genova et al. |
| 7,056,331 | B2 | 6/2006 | Kaplan et al. |
| 7,225,512 | B2 | 6/2007 | Genova et al. |
| 7,226,468 | B2 | 6/2007 | Ruff |
| 8,015,678 | B2 * | 9/2011 | Genova ............ A61B 17/06166 29/7.1 |
| 8,020,263 | B2 | 9/2011 | Genova et al. |
| 8,028,388 | B2 | 10/2011 | Genova et al. |
| 8,726,481 | B2 | 5/2014 | Maiorino et al. |
| 2003/0041426 | A1 | 3/2003 | Genova et al. |
| 2003/0149447 | A1 | 8/2003 | Morency et al. |
| 2004/0060409 | A1 | 4/2004 | Leung et al. |
| 2004/0060410 | A1 | 4/2004 | Leung et al. |
| 2004/0088003 | A1 | 5/2004 | Leung et al. |
| 2004/0226427 | A1 | 11/2004 | Trull et al. |
| 2004/0237736 | A1 | 12/2004 | Genova et al. |
| 2005/0267531 | A1 | 12/2005 | Ruff et al. |
| 2006/0111734 | A1 | 5/2006 | Kaplan et al. |
| 2006/0111742 | A1 | 5/2006 | Kaplan et al. |
| 2006/0135994 | A1 | 6/2006 | Ruff et al. |
| 2006/0135995 | A1 | 6/2006 | Ruff et al. |
| 2007/0005109 | A1 | 1/2007 | Popadiuk et al. |
| 2007/0065663 | A1 | 3/2007 | Trull et al. |
| 2007/0187861 | A1 | 8/2007 | Genova et al. |
| 2007/0224237 | A1 | 9/2007 | Hwang et al. |
| 2007/0257395 | A1 | 11/2007 | Lindh |
| 2008/0058869 | A1 | 3/2008 | Stopek et al. |
| 2008/0082113 | A1 | 4/2008 | Bishop |
| 2008/0195147 | A1 | 8/2008 | Stopek |
| 2008/0221618 | A1 | 9/2008 | Chen |
| 2008/0255611 | A1 | 10/2008 | Hunter |
| 2008/0281357 | A1 | 11/2008 | Sung |
| 2008/0312688 | A1 | 12/2008 | Nawrocki |
| 2009/0140012 | A1 | 6/2009 | Greer, Jr. |
| 2009/0248066 | A1 | 10/2009 | Wilkie |
| 2009/0287245 | A1 | 11/2009 | Ostrovsky |
| 2010/0023055 | A1 | 1/2010 | Rousseau |
| 2010/0084780 | A1 | 4/2010 | Lindh, Sr. |
| 2011/0046669 | A1 | 2/2011 | Goraltchouk |
| 2011/0125188 | A1 | 5/2011 | Goraltchouk |
| 2011/0288583 | A1 | 11/2011 | Goraltchouk |
| 2012/0046675 | A1 | 2/2012 | Bishop |

FOREIGN PATENT DOCUMENTS

| | | | |
|---|---|---|---|
| WO | WO03/017850 | | 3/2003 |
| WO | WO2007/131019 | A2 | 11/2007 |
| WO | WO2008/042992 | A2 | 4/2008 |
| WO | WO2008/112417 | A2 | 9/2008 |
| WO | 2008117328 | A2 | 10/2008 |
| WO | WO2008/011738 | | 10/2008 |
| WO | WO2008/141034 | A1 | 11/2008 |
| WO | WO2008/157142 | A2 | 12/2008 |
| WO | WO2009/020795 | A1 | 2/2009 |
| WO | WO 2009/105663 | A2 | 8/2009 |
| WO | WO 2009/129251 | A2 | 10/2009 |
| WO | WO2009/132284 | A2 | 10/2009 |
| WO | WO2009/140012 | A1 | 11/2009 |

OTHER PUBLICATIONS

European Search Report EP 12 16 5912 dated Jul. 18, 2012.

European Search Report EP 12 16 5938 dated Jan. 22, 2013.

European Search Report EP 12 16 9370 dated Sep. 12, 2012.

Canadian Office Action issued in corresponding Canadian Appln. No. 2,699,160 dated Mar. 3, 2016.

Chinese Office Action issued in corresponding Chinese Appln. No. 2014104126009 dated Dec. 2, 2015.

* cited by examiner

SYSTEM AND METHOD FOR FORMING BARBS ON A SUTURE

CROSS-REFERENCE TO RELATED APPLICATIONS

This application is a continuation of U.S. patent application Ser. No. 13/847,207 filed Mar. 19, 2013, now U.S. Pat. No. 8,966,728, which is a continuation of U.S. patent application Ser. No. 12/726,871 filed Mar. 18, 2010, now U.S. Pat. No. 8,402,621, which claims benefit of U.S. Provisional Application No. 61/173,723 filed Apr. 29, 2009, and the disclosures of each of the above-identified applications are hereby incorporated by reference in their entirety.

BACKGROUND

Technical Field

The present disclosure relates to medical sutures having barbs formed thereon. More particularly, the present disclosure relates to a system and method of forming barbs on sutures.

Background of Related Art

Barbed sutures are generally made of the same materials as conventional sutures and offer several advantages for closing wounds compared with conventional sutures. A barbed suture includes an elongated body that has one or more spaced barb, that project from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in cosmetic, laparoscopic and endoscopic procedures. The number of barbs called for on a particular suture may be influenced by the size of the wound and the strength required to hold the wound closed. Like a conventional suture, a barbed suture may be inserted into tissue using a surgical needle.

In some circumstances, a random configuration of barbs on the exterior surface of the suture is preferred to achieve optimal wound closure holding for the particular wound. However, in other circumstances, where the wound or tissue repair needed is relatively small, a reduced number of barbs may be desired. In other circumstances, a two-way barbed suture is desirable where the barbs permit passing of the suture in one direction over a portion of the suture and barbs permitting passing of the suture in a second direction over another portion of the suture to perform a tight closing stitch.

Various methods of forming barbs on sutures have been proposed such as mechanical cutting, laser cutting, injection molding, stamping, extrusion and the like. Such methods may be difficult or costly to achieve the desired result with respect to getting the arrangement of barbs in a configuration needed for the appropriate procedure and for doing so in an efficient cost effective manner. Conventional cutting methods of forming barbs have significant drawbacks in their ability to maintain sharpness, move rapidly, part cost and have slow manufacturing cycle time.

Accordingly, there is a continuing need for a system and method of forming barbs on a suture that is less difficult, more effective and economical.

SUMMARY

A station for cutting a barb suture is provided. The barb cutting station includes a suture transport assembly for supporting a first suture, a first knife assembly for forming barbs on the first suture, and a first clamp and position assembly for approximating the first suture towards the first knife assembly. The barb cutting station may further include a first suture cutting mechanism configured for severing the at least first suture when a defect is detected. The station may also include a first visual inspection assembly configured for detecting defective barbs.

The suture transport assembly, the first knife assembly and the first clamp and positioning assembly may be mounted to a base panel. The base panel may be mounted within a cabinet. The first knife assembly may include an ultrasonic mechanism for ultrasonically vibrating a blade extending therefrom. The first clamp and position assembly includes a gripping assembly for selectively gripping the first suture. The suture transport assembly may include an adjustment mechanism. The suture transport assembly may include a first pair of rotary motors configured to rotate the first suture along its longitudinal axis. The suture transport assembly may include a first tensioning cylinder configured to provide tension to the first suture.

Also provided is a method of forming a first barbed suture. The method includes providing a suture forming station including a suture transport assembly, a first knife assembly, and a first clamp and position assembly. The method further includes positioning a suture on the suture transport assembly, aligning the suture transport assembly with the knife assembly, activating the first knife assembly, advancing the suture transport assembly while simultaneously approximating the first clamp and position assembly towards the first knife assembly to engage the suture with the first knife assembly to form a barb, and retracting the first clamp and position assembly away from the first knife assembly. Retraction of the first clamp and position assembly may cause the deflection of the barb away from a longitudinal axis of the suture.

The barb forming method may further include the step of advancing the suture transport assembly relative to the first knife assembly to prepare the suture for a subsequent engagement with the knife assembly. The method may also include the steps of advancing the suture transport assembly and approximating the first clamp and position assembly towards and away from the knife assembly, one or more times to form additional barbs on the suture. The suture transport assembly of the barb forming method may be configured to receive a pair of sutures.

BRIEF DESCRIPTION OF THE DRAWINGS

Various embodiments of the present disclosure will be described herein below with reference to the figures wherein.

DETAILED DESCRIPTION

Figure 1:
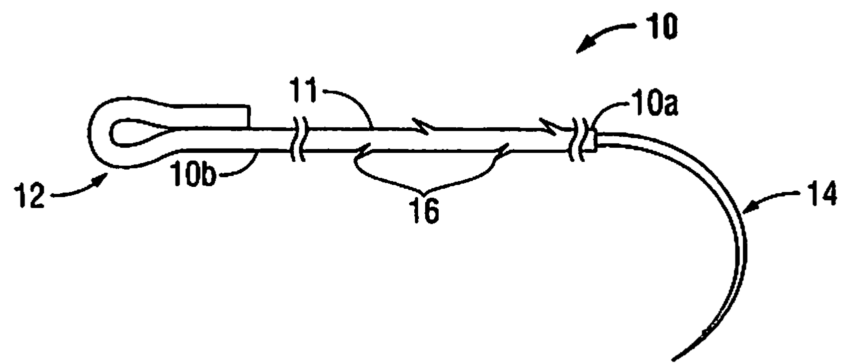
FIG. 1 is a perspective view of a barbed suture formed in accordance with the present disclosure.

A system and method for forming a barbed suture is herein described. Referring initially to FIG. 1, a barbed suture formed in accordance with the method of the present disclosure is shown generally as barbed suture 10. Suture 10 is formed from a monofilament thread 11, however, it is envisioned that suture 10 may be formed braided threads, multifilament threads and other surgical fibers. Although shown having a circular cross-sectional geometry, the cross-sectional geometry of thread 11 may be of any suitable shape. For example, thread 11 may be round, elliptical, square, flat, octagonal, and rectangular. Thread 11 may be formed of degradable materials, non-degradable materials, and combinations thereof. Thread 11 may be formed using any technique within the purview of those skilled in the art, such as, for example, extrusion, molding and/or solvent casting.

Figure 2:
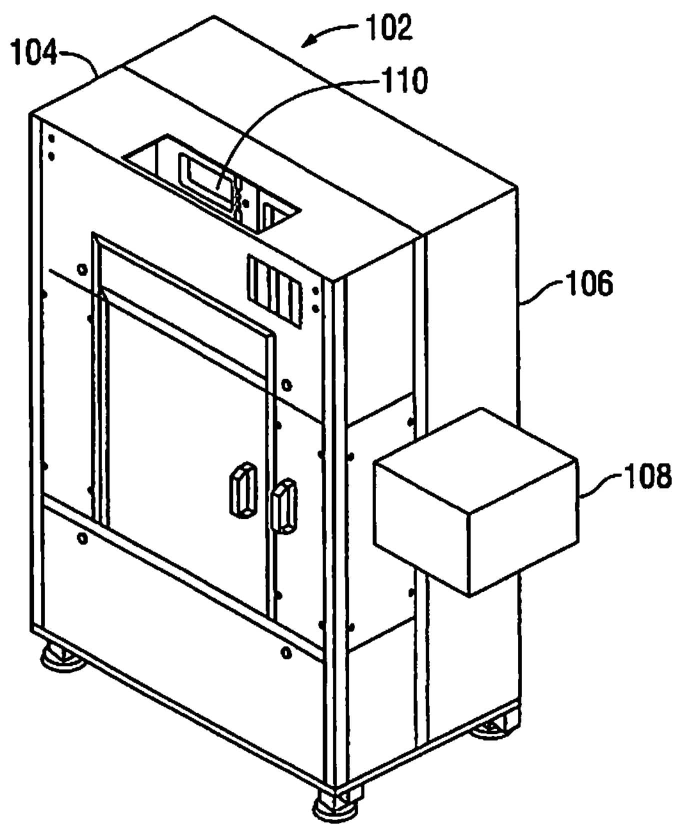
FIG. 2 is a perspective view of a cabinet of a barb cutting station according to an embodiment of the present disclosure.

Still referring to FIG. 1, barbed suture 10 includes a loop 12 formed on a distal end 10*b* thereof. Loop 12 is configured to facilitate attachment of distal end 10*b* of thread 11 with barb cutting station 100 (FIG. 2). Loop 12 may be formed in any manner and may be of any size and configuration. It is envisioned that barb cutting station 100 may be modified such that thread 11 may be attached thereto without loop 12. Optionally, barbed suture 10 includes a suture needle 14 attached to a proximal end 10*a* thereof. Needle 14 may be attached to thread 11 prior to or upon completion of the barb forming process. Formed on thread 11 between loop 12 and suture needle 14 are a plurality of radially spaced barbs 16. As will be discussed in greater detail below, barbs 16 may formed in any number, size, configuration, spacing and/or orientation.

With reference now to FIGS. 2-7, a system for forming barbed suture 10 will be described and is shown generally as barb cutting station 100. Referring initially to FIG. 2, barb cutting station 100 includes a cabinet 102 having a first housing 104, a second housing 106, and a control box 108. First housing 104 is configured to receive a base panel 110. Electric components (not shown) are maintained within second housing 106. Control box 108 is configured for controlling operation of cutting station 100. Although shown as a single unit, it is envisioned that first and second housings 104, 106 and/or control box 108 may arranged independent of one another. In this manner, cutting station 100 may be operated remotely.

Figure 3:
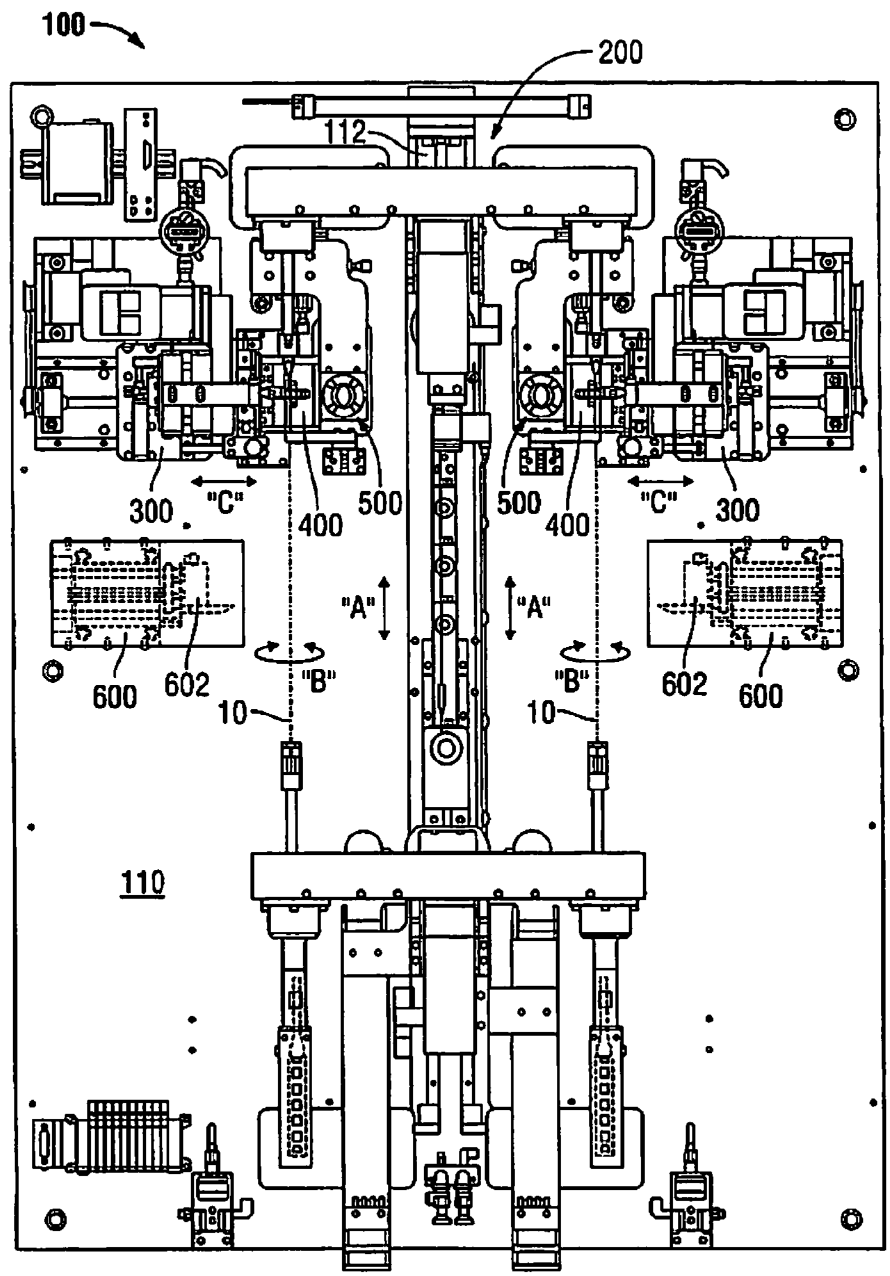
FIG. 3 is a schematic view of a base panel of the barb cutting station of FIG. 2.

Turning now to FIG. 3, maintained within cabinet 102 (FIG. 2) and mounted on base panel 110 are a suture transport assembly 200, a pair of knife assemblies 300, and a pair of clamp and position assemblies 400. Optionally, mounted to base panel 110 are a pair of suture cutting mechanisms 600 and/or a pair of visual inspection assemblies 500.

With reference still to FIG. 3, suture transport assembly 200 is mounted to base panel 110 in an upright position along a track 112. Suture transport assembly 200 is configured to support a pair of sutures 10 during the barb forming process. Suture transport assembly 200 is configured to move linearly along track 112 perpendicular to knife assemblies 300, in the direction of arrows "A".

Figure 4:
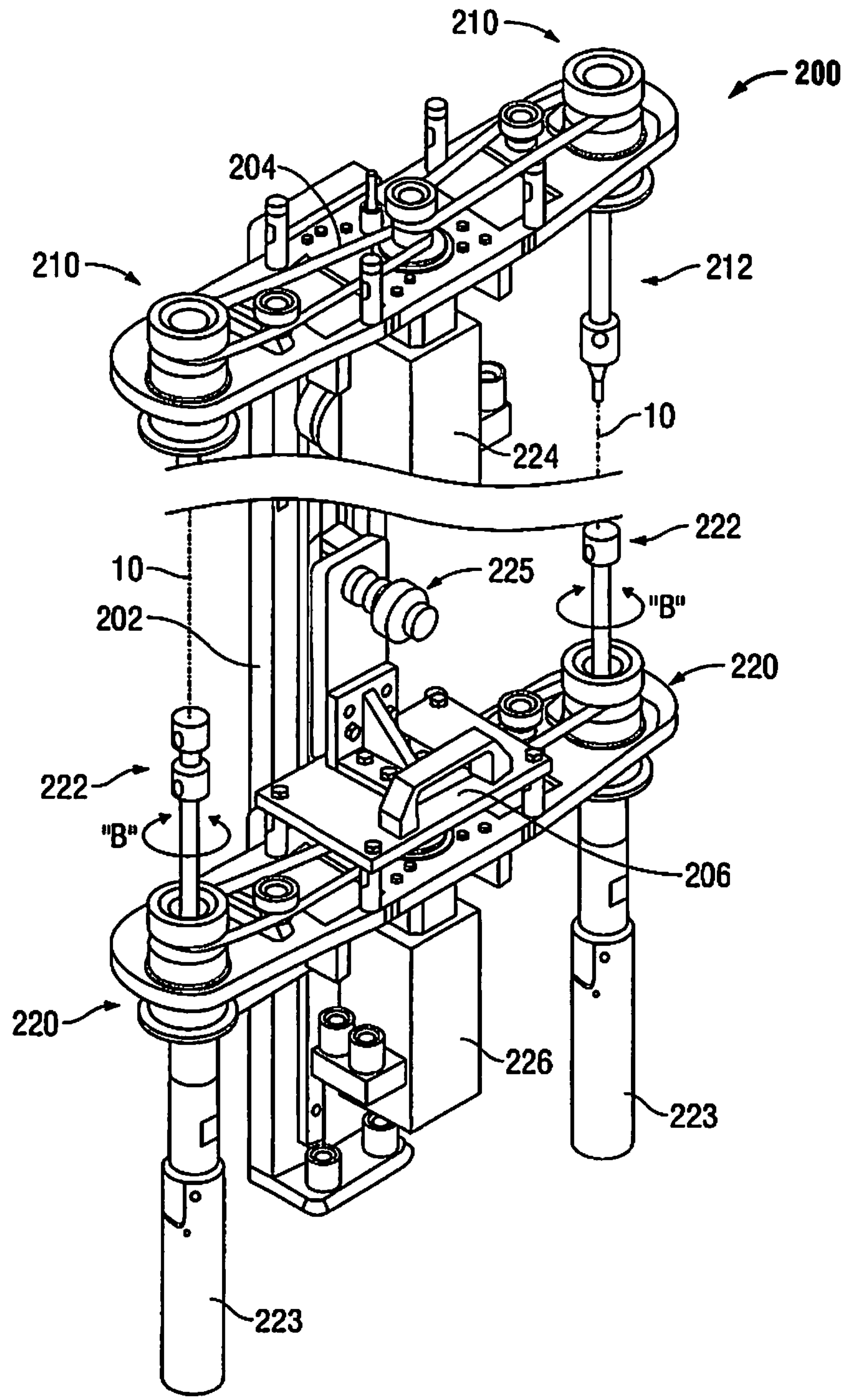
FIG. 4 is a perspective view of a suture support assembly of the barb cutting station of FIG. 2.

Turning now to FIG. 4, suture transport assembly 200 includes a base member 202, a fixed upper support member 204 and an adjustable lower support member 206. Fixed upper support member 204 includes a pair of rotary assemblies 210 each including a pin assembly 212 extending therefrom for engaging loops 12 formed on distal ends 10*b* of respective sutures 10. As discussed above, in an alternative embodiment, support member 204 are configured to engage sutures 10 without the use of loops 12. In this manner, each of support members 204 may include a clamp or anchor (not shown) for attachment of distal ends 10*b* of sutures 10 thereto.

Still referring to FIG. 4, adjustable lower support member 206 includes a pair of rotary assemblies 220 each including a needle holding assembly 222 extending therefrom for engaging proximal ends 10*a* (FIG. 1) of respective sutures 10. Holding assemblies 222 may include a clamp, anchor or other fixation device suitable for attachment with proximal ends 10 of sutures 10. Rotary assemblies 220 each further include a tensioning cylinder 223 for tensioning sutures 10 once sutures 10 have been received between respective pin assemblies 212 and needle holding assemblies 222. Tensioning cylinders 223 may be hydraulic, pneumatic, spring-load or otherwise configured to provide tension to sutures 10. Lower support member 206 further includes an adjustment mechanism 225 for adjusting the distance between lower support member 206 and upper support member 204. In this manner, suture transport assembly 200 may accommodate sutures 10 of various lengths. Each of upper and lower support members 204, 206 further includes a rotary motor 224, 226, respectively, operably connected to rotary assemblies 210, 220, respectively, for rotating sutures 10 along longitudinal axis thereof, in the direction of arrows "B".

Figure 5:
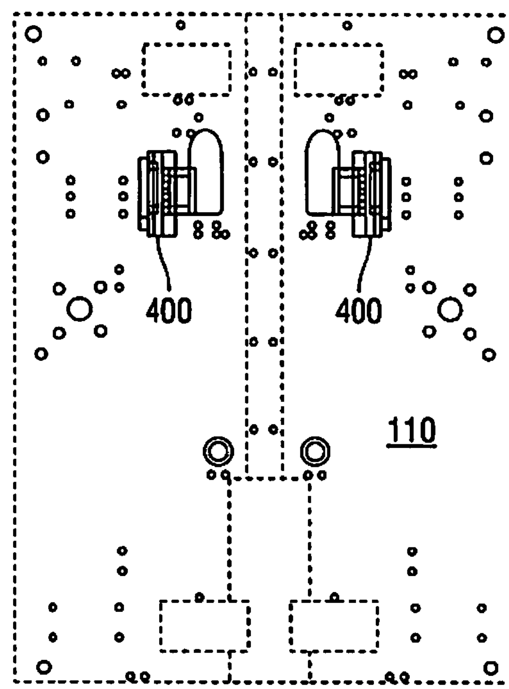
FIG. 5 a schematic view of a pair of clamp and position assemblies of the barb cutting station of FIG. 2 showing their respective locations on the base panel.

Referring briefly back to FIG. 3, knife assemblies 300 are fixedly mounted to base panel 110 adjacent suture transport assembly 200. Knife assemblies 300 are configured for cutting barbs 16 (FIG. 1) in sutures 10. Turning now to FIG. 5, each of knife assemblies 300 includes a base 302 and a cutting assembly 304 operably mounted to base 302. Each of cutting assemblies 304 include a cutting member 306 extending outwardly therefrom and include a blade 308 for cutting barbs in sutures 10. As shown, knife assemblies 300 include an ultrasonic mechanism 312 for ultrasonically vibrating blade 308. Alternatively, knife assemblies 300 may include a heating element or other suitable mechanism (not shown) for heating blade 308. By vibrating or heating blade 308, the force necessary to cut barbs 16 is reduced.

Still referring to FIG. 5, each of cutting assemblies 304 further includes a rotary mechanism 310 for rotating cutting members 306. Rotary mechanism 310 is configured to index blade 308 during the barb forming process to adjust the angle of cut. Blade 308 may further be rotated at least one-hundred and eighty degrees (180°) such that each surface of blade 308 may be used. In one embodiment, rotation of blade 308 occurs only after the desired number of barbs 16 have been formed along the desired length of sutures 10. Cutting assemblies 304 are mounted to bases 302 such that cutting members 306 may be advanced, in the direction of arrows "C". In this manner, cutting assemblies 222 may be retracted once the barb forming process is completed to permit reloading and repositioning of suture transport assembly 200. Cutting assemblies 304 remain stationary or in a fixed position during the cutting of sutures 10 to form barbs 16. In this manner, blades 308 are not moved into contact with the suture, instead clamp and position assemblies 400 move suture 10 into contact with blades 308.

Figure 6:
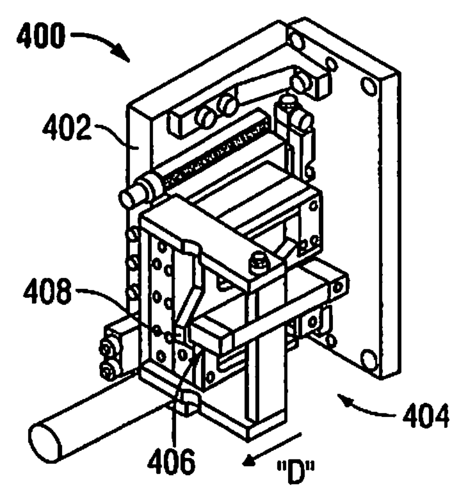
FIG. 6 is a perspective view of the clamp and position assembly of FIG. 5.
Figure 7:
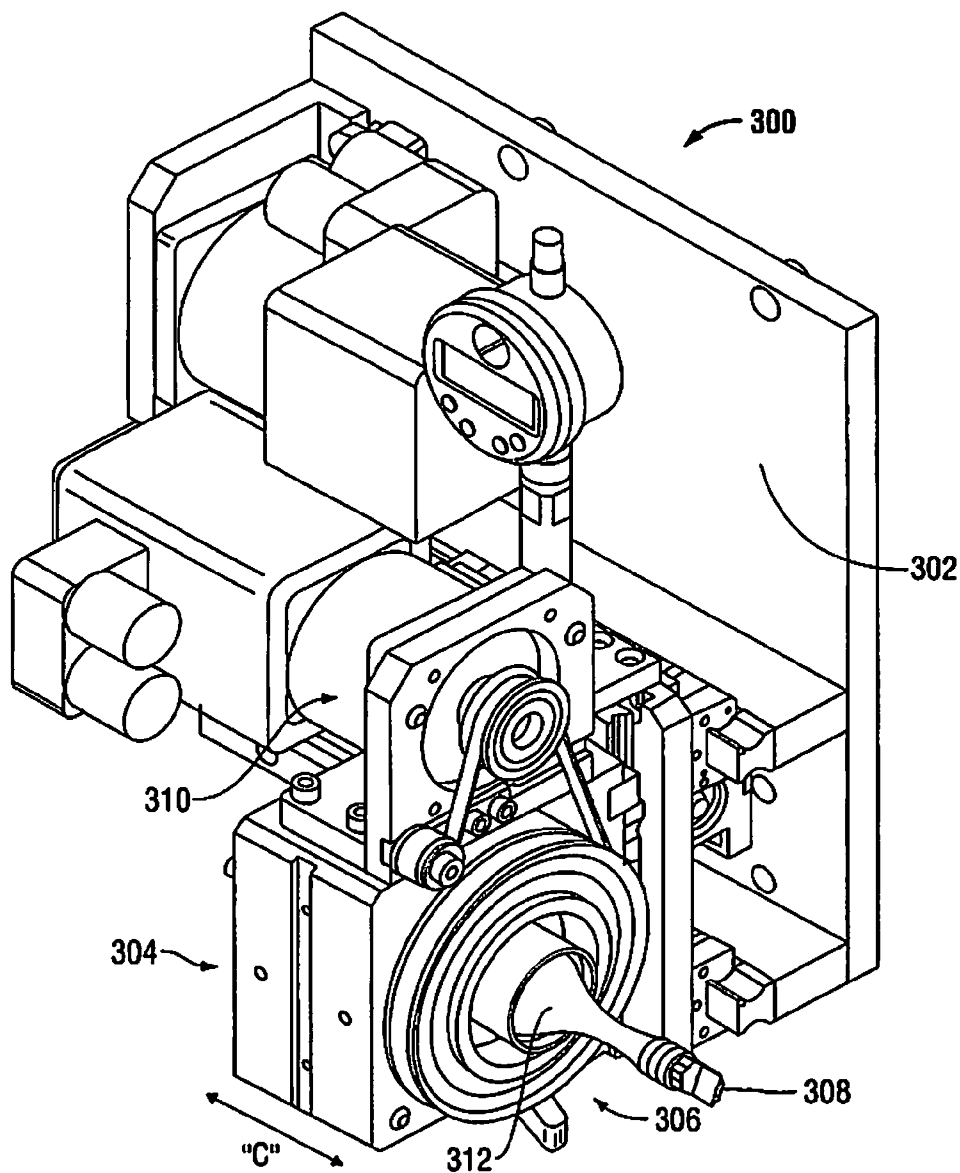
FIG. 7 is a perspective view of a knife assembly of the barb cutting station of FIG. 2.

Turning to FIGS. 3 and 6, clamp and position assemblies 400 are securely mounted to base panel 110 adjacent suture transport assembly 200 and respective ultrasonic knife assemblies 300. Clamp and position assemblies 400 are configured for approximating sutures 10 towards and away from ultrasonic knife assembly 300. Turning now to FIG. 7, each of clamp and position assemblies 400 includes a stationary base 402 and a moveable carriage 404. Carriage 404 includes a gripper assembly 406 for selectively gripping suture 10 during the barb forming process. Gripper assembly 406 includes an anvil portion 408 for supporting suture 10 as carriage 404 is approximated towards cutting member 306 of knife assembly 300 and as suture 10 engages blade 308.

With reference back to FIG. 2, visual inspection assemblies 500 are configured for monitoring the cutting of barbs 16. In the event that a misformed or defective barb is cut, visual inspection assembly 500 is configured to signal cutting mechanism 600 to sever the defective suture, such that that suture may not be used.

With reference still to FIG. 2, cutting mechanism 600 is configured for cutting suture 10 in the event that a defective barb is detected by visual inspection assembly 500. Cutting mechanism 600 may further be configured for manual actuation by an operator. Cutting mechanism 600 may include any device capable of selectively severing suture 10 during the barb forming process. Cutting mechanism 600 may include a blade 602, or a laser, a heating element or other suitable device (not shown).

The operation of the suture cutting station 100 will now be described with reference to FIGS. 2-7. Initially, cabinet 102 is opened to access base panel 110. Suture transport assembly 200 is then adjusted using adjustment mechanism 225 to configure upper and lower support members 204, 206 to accommodate sutures 10 of a given length. Sutures 10 are next secured to suture transport assembly 200 by hooking loops 12 formed on distal ends 10*b* of sutures 10 about pin assemblies 212 of fixed upper support member 204 and fastening armed proximal ends 10*a* of sutures 10 within needle holding assemblies 222 of lower support member 206. Tensioning cylinders 223 within rotary assemblies 220 ensure that sutures 10 are properly tensioned between pin and needle holding assemblies 212, 222, respectively. Suture transport assembly 200 is then positioned such that blades 308 of cutting member 306 are aligned near proximal ends 10*a* of sutures 10.

Once suture transport assembly 200 is properly positioned with respect to ultrasonic knife assemblies 300, cutting assemblies 304 of knife assemblies 300 are advanced in the direction of arrows "C" (FIG. 3), such that blades 308 of cutting assemblies 306 are positioned outwards of and in close approximation to (but not in contact with) sutures 10. Knife assemblies 300 are then activated to cause the ultrasonic vibrating or heating of blades 308. Once knife assemblies 300 have been activated, cutting assembly 304 remains stationary during the barb forming process and suture transport assembly 200 and clamp and position assemblies 400 operate in unison to move sutures 10 relative to blade 308 to form barbs 16 (FIG. 1) along the lengths thereof.

Figure 8:
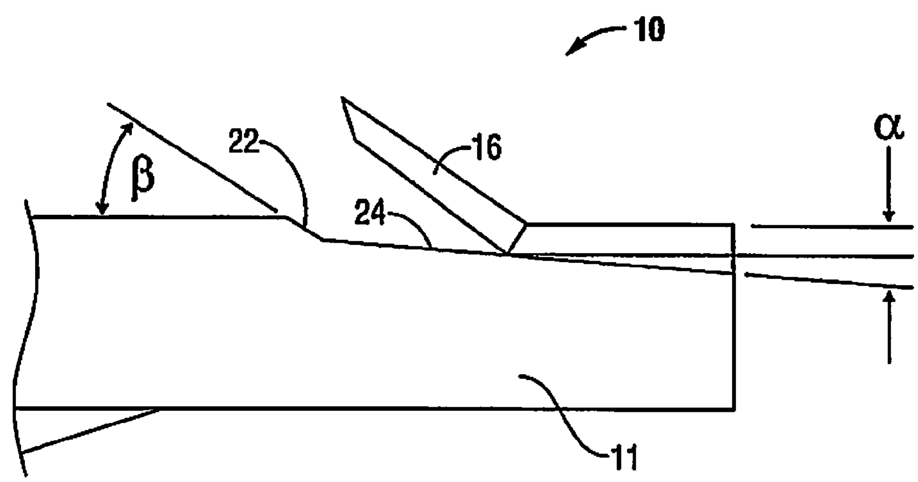
FIG. 8 is a side sectional view of a barbed portion of the barbed suture of FIG. 1.

With reference to FIG. 8, barbs 16 are formed in two steps. A first portion 22 of the cut is made at an angle ("β") of from about thirty to about forty degrees (30°-40°) with respect to the surface of the suture to a predetermined depth. In this manner, clamp and position assemblies 400 are approximated towards blades 308 (arrow "D") while suture transport assembly 200 advances sutures 10 longitudinally (arrow "A"). The angle of cut is then adjusted for the second portion 24 to an angle ("α") of from about two to about eight degrees (2°-8°) with respect to the surface or longitudinal axis of suture 10 by varying the rate of movement of clamp and position assemblies 400 and suture transport assembly 200 relative to each other and blade 308.

Upon completion of the second cut, clamp and position assemblies 400 are approximated away from cutting assemblies 304 thereby causing blades 308 to engage, and thus, flex barbs 16 outwardly. Sutures 10 are then released from gripper assemblies 406 as clamp and position assemblies 400 continue to move away from cutting assemblies 304 to permit suture 10 to be repositioned for the next cut. Suture transport assembly 200 then advances sutures 10 relative to cutting assemblies 306 as rotary assemblies 210, 220 rotate sutures 10 along longitudinal axis thereof to ready sutures 10 for the next cut. Depending on the desired configuration of barbs 16 along a length thereof, rotary assemblies 210, 220 may be configured to rotate sutures 10 from zero degrees (0°) thru three-hundred sixty degrees (360°) along a length thereof.

Additional barbs 16 are formed in the manner described above. This process continues until barbs 20 are formed along the desired lengths of sutures 10. Knife assemblies 300 are then retracted to permit suture transport assembly 200 to return to an initial position. Sutures 10 are then unloaded and the barb forming process is complete.

During barb formation, visual inspection assemblies 500 (FIG. 3) monitor the characteristics of barbs 16. In the event a barb is detected that does not conform to the desired configuration, suture cutting mechanism 600 (FIG. 2) is activated, thereby severing suture 10 and terminating the barb forming process.

Barb cutting station 100 may be configured to cut barbs 16 in any suitable pattern, for example, helical, linear, or randomly spaced. The pattern may be symmetrical or asymmetrical. The number, configuration, spacing and surface area of the barbs may vary depending upon the tissue in which barbed suture 10 is used, as well as the composition and geometry of the material utilized to form suture 10. Additionally, the proportions of barbs 16 may remain relatively constant while the overall length and spacing thereof may be determined by the tissue being connected. For example, if barbed suture 10 is to be used to connect the edges of a wound in skin or tendon, barbs 16 may be made relatively short and more rigid to facilitate entry into this rather firm tissue. Alternatively, if barbed suture 10 is intended for use in fatty tissue, which is relatively soft, barbs 16 may be made longer and spaced further apart to increase the ability of the suture to grip the soft tissue.

The surface area of barbs 16 may also vary. For example, fuller-tipped barbs may be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In particular embodiments, a single directional suture may have both large and small barbs; in other embodiments a bi-directional suture may have both large and small barbs. The barbs formed may include geometrical shapes such as round, triangular, square, oblique, elliptical, octagonal, rectangular, and flat While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

The invention claimed is:

1. A barb cutting station comprising:

a suture transport assembly configured to engage a first end of a suture and a second end of a suture, the suture transport assembly including an upper support configured to engage a loop on the first end of the suture and a lower support configured to engage a needle on the second end of the suture;

a clamp and position assembly positioned to clamp a portion of the suture between the first end of the suture and the second end of the suture; and a knife assembly including a knife, the clamp and position assembly moveable to contact a portion of the suture between the first end of the suture and the second end of the suture with the knife to cut a barb into a surface of the suture.

2. The barb cutting station of claim 1, further including a visual inspection assembly configured for detecting defective barbs.

3. The barb cutting station of claim 2, further including a suture cutting mechanism configured for severing the suture supported by the suture transport assembly when a defect is detected.

4. The barb cutting station of claim 1, further comprising an ultrasonic mechanism for ultrasonically vibrating the knife.

5. The barb cutting station of claim 1, wherein the suture transport assembly includes an adjustment mechanism for adjusting a distance between the upper support and the lower support of the suture transport assembly.

6. The barb cutting station of claim 1, wherein the suture transport assembly includes a rotary motor configured to rotate the suture along a longitudinal axis of the suture.

7. The barb cutting station of claim 1, wherein the suture transport assembly includes a tensioning cylinder configured to provide tension to the suture.

8. The barb cutting station of claim 1, wherein the clamp and position assembly includes a gripping assembly for selectively gripping a portion of the suture between the first end of the suture and the second end of the suture.

9. The barb cutting station of claim 8, wherein the knife assembly is positioned to cut a barb into a surface of the suture adjacent the portion of the suture gripped by the gripping assembly.

10. The barb cutting station of claim 1, further comprising a heating element for heating the knife.

11. The barb cutting station of claim 1, wherein the suture transport assembly, knife assembly, and clamp and position assembly are mounted to a base panel.

12. The barb cutting station of claim 11, wherein the base panel is mounted within a cabinet.

13. The barb cutting station of claim 1, wherein the suture transport assembly includes an adjustment mechanism for adjusting the length of the suture.

14. The barb cutting station of claim 1, wherein the suture transport assembly includes a base member, fixed support member, and an adjustable support member.

15. The barb cutting station of claim 14, wherein the fixed support member includes a pair of rotary assemblies.

16. The barb cutting station of claim 14, wherein the fixed support member includes a pair of pin assemblies.

17. The barb cutting station of claim 1, wherein the upper support includes a plurality of rotary assemblies.

18. The barb cutting station of claim 1, wherein the lower support includes a plurality of rotary assemblies.

19. The barb cutting station of claim 1, further including a track, wherein the suture transport is configured to move linearly along the track.

* * * * *